US012589236B2

(12) United States Patent
Arfaee et al.

(10) Patent No.: US 12,589,236 B2
(45) Date of Patent: Mar. 31, 2026

(54) IMPLANTABLE ARTIFICIAL HEART

(71) Applicant: Stichting Amsterdam UMC, Amsterdam (NL)

(72) Inventors: Maziar Arfaee, Gouda (NL); Annemijn Vis, Amsterdam (NL); Jolanda Kluin, Den Dolder (NL)

(73) Assignee: Stichting Amsterdam UMC, Amsterdam (NL)

( * ) Notice: Subject to any disclaimer, the term of this patent is extended or adjusted under 35 U.S.C. 154(b) by 0 days.

(21) Appl. No.: 18/998,258

(22) PCT Filed: Jul. 27, 2023

(86) PCT No.: PCT/IB2023/057618
§ 371 (c)(1),
(2) Date: Jan. 24, 2025

(87) PCT Pub. No.: WO2024/023749
PCT Pub. Date: Feb. 1, 2024

(65) Prior Publication Data
US 2025/0262424 A1 Aug. 21, 2025

(30) Foreign Application Priority Data

Jul. 28, 2022 (EP) .................................... 22187505

(51) Int. Cl.
*A61M 60/196* (2021.01)
*A61M 39/24* (2006.01)
(Continued)

(52) U.S. Cl.
CPC .......... *A61M 60/196* (2021.01); *A61M 39/24* (2013.01); *A61M 60/268* (2021.01);
(Continued)

(58) Field of Classification Search
CPC .............. A61M 60/268; A61M 60/894; A61M 60/562; A61M 60/196; A61M 60/438; A61M 39/24
See application file for complete search history.

(56) References Cited

U.S. PATENT DOCUMENTS 3,668,708 A 6/1972 Tindal
3,827,426 A 8/1974 Page et al.
(Continued)

FOREIGN PATENT DOCUMENTS

DE 102020132268 B3 3/2022
WO 2021260614 A1 12/2021

*Primary Examiner* — Pamela M. Bays
(74) *Attorney, Agent, or Firm* — Banner & Witcoff, Ltd.

(57) ABSTRACT

Present disclosure discloses an implantable total artificial heart. The artificial heart includes a first pumping chamber, a second pumping chamber and an actuator disposed between the first pumping chamber and the second pumping chamber. The actuator is configured to operate between a first operating state and a second operating state. Further, the artificial heart includes a plurality of first wires wound around the first pumping chamber and the actuator, and/or a plurality of second wires wound around the second pumping chamber and the actuator. Each of the plurality of first and second wires are configured to compress the first and second pumping chambers relative to operation of the actuator for receiving fluid into and pumping fluid out of the first and second pumping chamber. The configuration of the artificial heart is compact, improves durability and mimicking the natural movement of a human tissue for reducing stress on blood and resulting in fewer side effects.

13 Claims, 8 Drawing Sheets

(51) Int. Cl.

| | |
|---|---|
| *A61M 60/268* | (2021.01) |
| *A61M 60/438* | (2021.01) |
| *A61M 60/562* | (2021.01) |
| *A61M 60/894* | (2021.01) |

(52) U.S. Cl.
CPC ........ *A61M 60/438* (2021.01); *A61M 60/562* (2021.01); *A61M 60/894* (2021.01); *A61M 2205/04* (2013.01); *A61M 2205/50* (2013.01); *A61M 2210/125* (2013.01)

(56) References Cited

U.S. PATENT DOCUMENTS

| | | | | |
|---|---|---|---|---|
| 5,300,111 | A * | 4/1994 | Panton | A61M 60/462 |
| | | | | 623/3.19 |
| 6,808,483 | B1 * | 10/2004 | Ortiz | A61B 17/00234 |
| | | | | 600/16 |
| 2008/0045777 | A1 | 2/2008 | Jassawalla et al. | |
| 2010/0298932 | A1 | 11/2010 | Sherif | |

* cited by examiner

IMPLANTABLE ARTIFICIAL HEART

RELATED APPLICATIONS

This application is a National Stage Application under 35 U.S.C. 371 of PCT application PCT/IB2023/057618 designating the United States and filed Jul. 27, 2023; which claims the benefit of EP application Ser. No. 22/187,505.7 and filed Jul. 28, 2022, each of which are hereby incorporated by reference in their entireties.

TECHNICAL FIELD

Present disclosure generally relates to an artificial heart and in particularly relates to an implantable artificial heart.

BACKGROUND

Heart failure is a clinical condition with symptoms that includes shortness of breath, lack of energy, swelling of ankles and the like. Progressively, severe heart failure situations include degradation of health through severe weight loss, muscle wasting, failure of other organs (particularly the kidneys or liver), compromised immune response and risk of infection and ultimately death. Generally, heart failure is triggered by impairment of pumping function of heart muscular tissue, leading to reduction in blood supply to tissues, organs and thereby deficient in supply of nutrients, particularly oxygen to the body.

Current treatments for heart failure are predominantly based on drugs and cardiac surgery remedies such as heart transplantation, bypass surgery etc. In particular, in drug-based treatments, some drugs have been found to be ineffective or even harmful, and drug therapy is of limited benefit for heart muscle that is severely damaged. Furthermore, the mortality of patients with heart failure has not changed. Other treatments include cardiac resynchronization therapy. The gold standard therapy for end-stage heart failure is heart transplantation, which is donor based. Due to the shortage in donor organs, a lot of patients are on the waiting list but will never receive an organ. Further, there is intensive research in the fields of cellular and gene therapies although their clinical application seems remote.

Considering the above, artificial hearts have been researched and developed which are configured to substitute functioning of the human heart. Mechanical circulatory support devices are mainly used to support one side of the heart (mostly the left side). These devices can be used as bridge-to-transplant or destination therapy. Biventricular heart failure requires assist or replacement of both cardiac ventricles ('total artificial heart'). Conventional total artificial hearts are structured to be implanted as a temporary treatment, as a bridging therapy to overcome the waiting time for a heart transplantation. Further, configuration of such artificial hearts is complex due to adapting of complex medical devices thereby limiting the use of artificial hearts as a permanent solution. In addition, conventional total artificial hearts pose biocompatibility issues, which results the blood to interact with rigid components, thereby leading to negative side effects such as thromboembolic events, risk of haemorrhagic events, which is undesired.

The present disclosure is directed to overcome one or more limitations stated above or any other limitations associated with the devices known in art.

SUMMARY OF THE DISCLOSURE

It is an objective to provide an implantable total artificial heart, which is compact, durable and mimicking the natural movement of human tissue for potentially reducing stress on the blood and resulting in fewer side effects.

To better address one or more of these concerns, in a first aspect of the disclosure there is provided an implantable total artificial heart [hereinafter referred as artificial heart]. The artificial heart includes a first pumping chamber defined with a first inlet and a first outlet. Further, the artificial heart includes a second pumping chamber positioned adjacent to the first pumping chamber and defined with a second inlet and a second outlet. Furthermore, the artificial heart includes an actuator disposed between the first pumping chamber and the second pumping chamber. The actuator is configured to operate between a first operating state and a second operating state. Additionally, the artificial heart includes a plurality of first wires wound around the first pumping chamber and the actuator, and/or a plurality of second wires wound around the second pumping chamber and the actuator. Each of the plurality of first wires and/or the second wires are configured to compress the first pumping chamber and/or the second pumping chamber, relative to operation of the actuator between the first operating state to the second operating state for receiving fluid into and pumping fluid out of the first pumping chamber and the second pumping chamber. The configuration of the artificial heart aids in improving durability of the artificial heart and mimicking the natural movement of a human tissue for potentially reducing stress on the blood and resulting in fewer side effects.

In an embodiment, the artificial heart includes at least one non-return valve disposed in each of the first inlet, the first outlet, the second inlet and the second outlet. The non-return valve facilitates in selective flow of fluid through the first inlet, the first outlet, the second inlet and the second outlet, based on operating sequence of the artificial heart.

In an embodiment, an outer surface of the first pumping chamber, the second pumping chamber and the actuator is defined with a plurality of channels. Each of the plurality of channels is configured to secure at least one first wire of the plurality of first wires and at least one second wire of the plurality of second wires. Further, each of the plurality of channels is configured to guide the at least one first wire and the at least one second wire, relative to operation of the actuator between the first operating state and the second operating state.

In an embodiment, the first operating state corresponds to a deflated condition of the actuator, relating to a decompressed state of the first pumping chamber and the second pumping chamber, for passive drawing of the fluid into the first pumping chamber and the second pumping chamber, and the second operating state corresponds to an inflated condition of the actuator, relating to a compressed state of the first pumping chamber and the second pumping chamber for pumping the fluid out of the first pumping chamber and the second pumping chamber.

In an embodiment, the first pumping chamber and the second pumping chamber are made of fluid tight, non-stretchable material. These materials aid the artificial heart in mimicking working of the natural heart and also improving durability of the artificial heart.

In an embodiment, an inner surface of the first pumping chamber and the second pumping chamber is made of biocompatible material, which contacts with the fluid. The biocompatible material aids in reducing complications when implanted inside the body.

In an embodiment, the artificial heart includes a pump fluidly coupled to the actuator, wherein the pump is configured to selectively operate the actuator between the first operating state and the second operating state in a pulsating manner.

In an embodiment, the artificial heart includes a control unit communicatively coupled to the pump, wherein the control unit is configured to control actuation of the pump to provide pulsatile flow of the driving fluid to the actuator.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF ACCOMPANYING DRAWINGS

The invention is as set forth in the appended claims, while encompassing various modifications routine to the skilled person and claim equivalents. The disclosure itself, as well as a mode of use, further objectives, and advantages thereof, will best be understood by reference to the following detailed description of the embodiments when read in conjunction with the accompanying drawings. One or more embodiments are now described, by way of example only, with reference to the accompanying exemplary drawings wherein like reference numerals represent like elements and in which:

The figures depict embodiments of the disclosure for purposes of illustration only. One skilled in the art will readily recognize from the following description that alternative embodiments of the structures and methods illustrated herein may be employed without departing from the principles of the disclosure described herein.

DETAILED DESCRIPTION

While embodiments in the disclosure are subject to various modifications and alternative forms, specific embodiments thereof have been shown by way of example in the figures and will be described below. It should be understood, however, that it is not intended to limit the disclosure to the particular forms disclosed, but on the contrary, the disclosure is to cover all modifications, equivalents, and alternatives falling within the scope of the disclosure.

It is to be noted that a person skilled in the art would be motivated from the present disclosure and modify various features of an implantable artificial heart. Therefore, such modifications are part of the disclosure. Accordingly, the drawings show only those specific details that are pertinent to understand the embodiments of the present disclosure, so as not to obscure the disclosure with details that will be readily apparent to those of ordinary skilled in the art having benefit of the description herein.

The terms "comprises", "comprising", or any other variations thereof used in the disclosure, are intended to cover a non-exclusive inclusions, such that implantable artificial heart that comprises a list of components does not include only those components but may include other components not expressly listed or inherent to such device. In other words, one or more elements in a device proceeded by "comprises . . . a" does not, without more constraints, preclude the existence of other elements or additional elements in the system or device.

In the following detailed description, embodiments of the disclosure are explained with reference to accompanying figures that form a part hereof, and which are shown by way of illustration and specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

Figure 1:
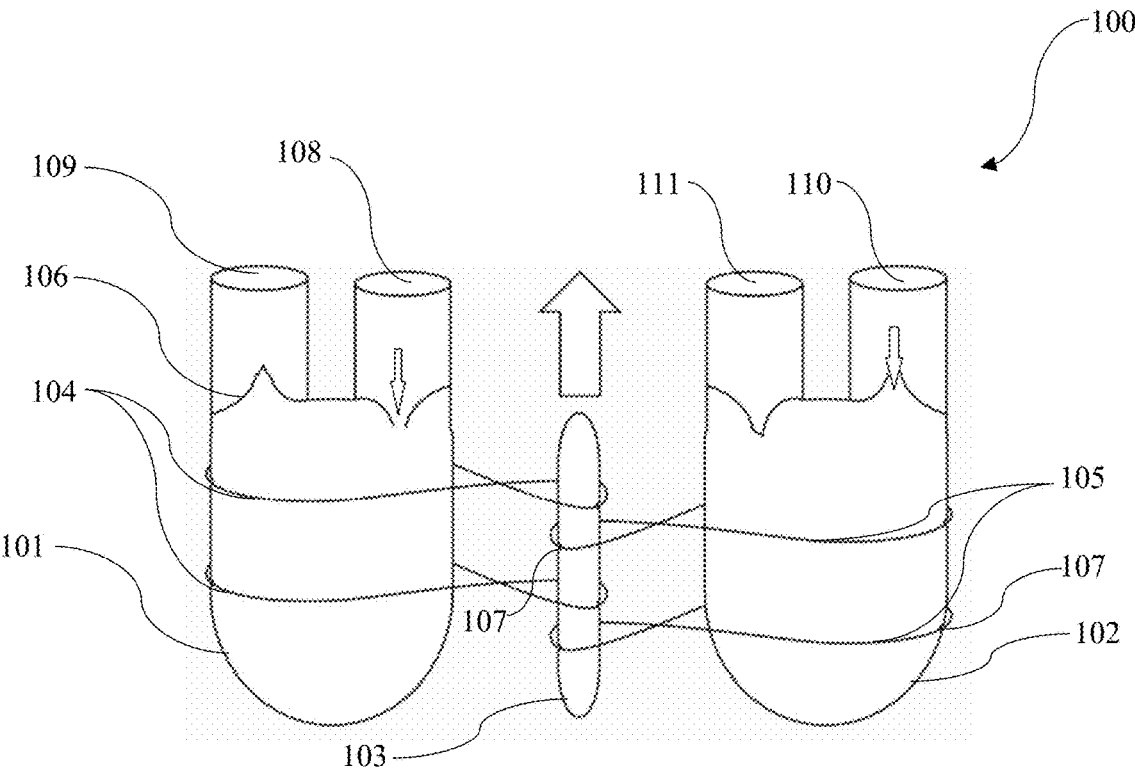
FIG. 1 illustrates a schematic view of an implantable artificial heart, depicting a first operating state of an actuator, in accordance with an embodiment of the present disclosure.

FIG. 1 illustrates a schematic view of the implantable total artificial heart (100) [hereinafter referred as artificial heart]. The artificial heart (100) may be implantable in the circulatory system of a human body. The artificial heart (100) may include a first pumping chamber (101) and a second pumping chamber (102), which are positioned adjacent to each other. The first pumping chamber (101) may be defined with a first inlet (108), a first outlet (109), and the second pumping chamber (102) may be defined with a second inlet (110) and a second outlet (111). The first inlet (108) and the second inlet (110) may be configured to allow flow of fluid into the first pumping chamber (101) and the second pumping chamber (102), respectively. Here the flow of fluid may refer to blood and blood vessels which aids in blood circulation throughout the body of a subject (thus, patient). Further, the first outlet (109) and the second outlet (111) may be configured to allow flow of fluid out of the first pumping chamber (101) and the second pumping chamber (102), respectively. In an embodiment, the first pumping chamber (101) and the second pumping chamber (102) may be made of fluid tight, soft non-stretchable materials, and the inner surface which contacts with the fluid (thus, the blood) may be made of biocompatible material, which may exhibit similar properties as that of a human tissue. As an example, the soft non-stretchable materials may be but not limiting to woven Goretex (as used in clinically applied aortic grafts), woven Dyneema fibers and the like. The size of the first pumping chamber (101) and the second pumping chamber (102) of the artificial heart can be customised to the need of a subject (thus, patient). In an illustrated embodiment, the first pumping chamber (101) and the second pumping chamber (102) includes a U-shaped cross-section profile and the same cannot be construed as a limitation, since the first pumping chamber (101) and the second pumping chamber (102) may include any geometrical profile or cross-section, based on the requirement.

Figure 2:
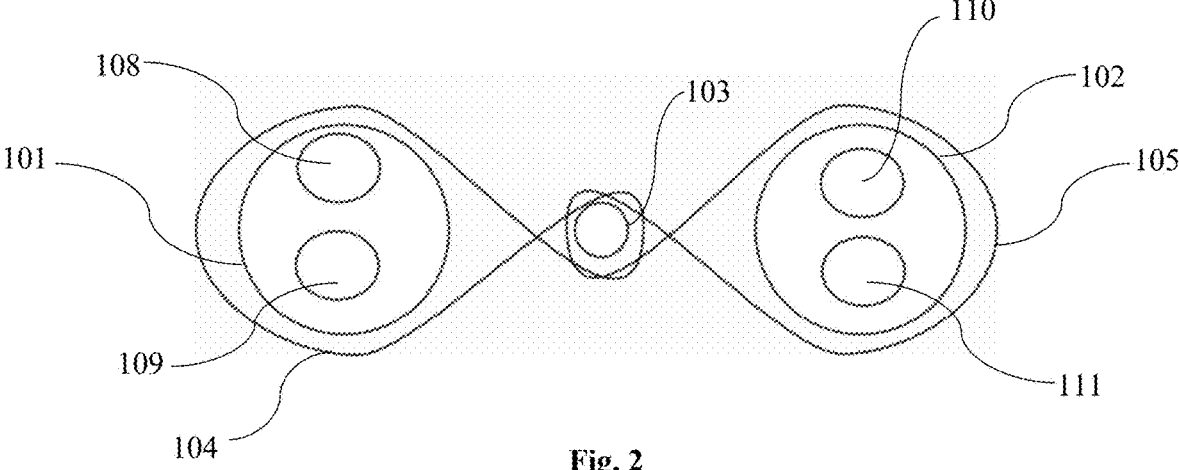
FIG. 2 illustrates a top view of the implantable artificial heart of FIG. 1.
Figure 3:
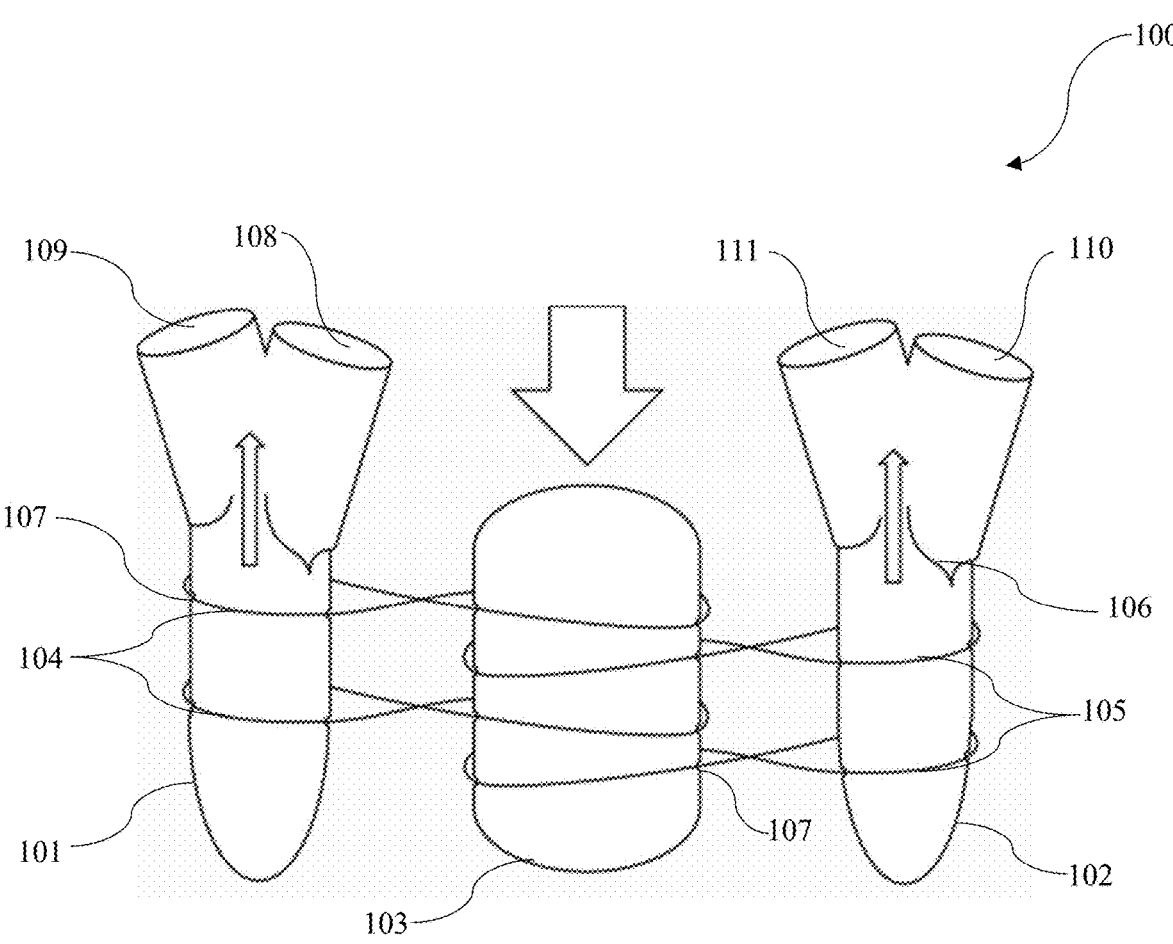
FIG. 3 illustrates a schematic view of the implantable artificial heart, depicting a second operating state of the actuator, in accordance with an embodiment of the present disclosure.

As apparent from FIG. 1, further the artificial heart (100) may include at least one non-return valve (106) disposed in each of the first inlet (108), the first outlet (109), the second inlet (110) and the second outlet (111). The at least one non-return valve (106) may be selectively operated such that, during flow of the fluid into the first pumping chamber (101) and the second pumping chamber (102), the non-return valves (106) disposed at the first inlet (108) and the second inlet (110) are structured to open and the non-return valves (106) disposed at the first outlet (109) and the second outlet (111) are closed and vice-versa. In an embodiment, the at least one non-return valve (106) may operate passively based on pressure acting on the non-return valve (106). As an example, the at least one non-return valve (106) may close, when the pressure after the at least one non-return valve is higher than the pressure before it and vice-versa. In an illustrated embodiment, one non-return valve is disposed in each of the first inlet (108), the first outlet (109), the second inlet (110) and the second outlet (111). However, the same cannot be construed as a limitation since more than one non-return (106) may be disposed in each of the first inlet (108), the first outlet (109), the second inlet (110) and the second outlet (111). As an example, the at least one non-return valve (106) may be but not limited to a biological or mechanical valve that is clinically used. Furthermore, the artificial heart (100) may include an actuator (103), which may be disposed between the first pumping chamber (101) and the second pumping chamber (102). The actuator (103) may be configured to operate between a first operating state and a second operating state. In an illustrated embodiment, as seen in FIG. 1 and FIG. 3, the actuator (103) is defined to include a cylindrical profile and the same cannot be considered as a limitation, since the actuator (103) may include any other geometrical profile based on the requirement. In an embodiment, the first operating state may correspond to deflated condition [as seen in FIG. 1] of the actuator (103) and the second operating state may correspond to inflated condition [as best seen in FIG. 2] of the actuator (103). In an embodiment, the artificial heart (100) may include a pump [not shown in Figs] which may be fluidly coupled to the actuator (103). The pump may be configured to channelize a driving fluid such as liquid or air of medical grade, out of and into the actuator (103) for operating the actuator (103) to the first operating state and the second operating state, respectively.

Figure 4:
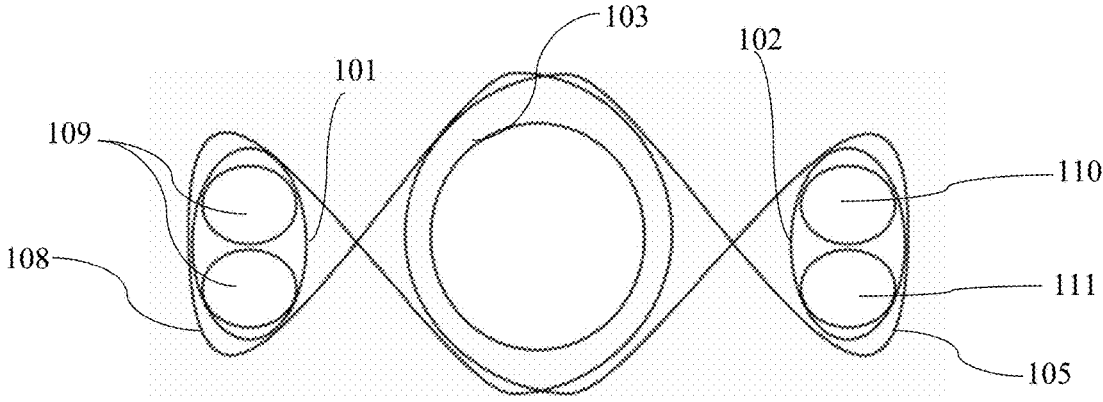
FIG. 4 illustrates a top view of the implantable artificial heart of FIG. 3.

Further referring to FIG. 1, the artificial heart (100) may include a plurality of first wires (104) and a plurality of second wires (105). The plurality of first wires (104) are wound around the first pumping chamber (101) and the actuator (103), and the plurality of second wires (105) are wound around the second pumping chamber (102) and the actuator (103). In an illustrated embodiment, as best seen in FIGS. 2 and 4 the plurality of first wires (104) and the plurality of second wires (105) are wound around the first pumping chamber (101), the second pumping chamber (102) and the actuator (103) in a criss-cross configuration, where the plurality of first wires (104) and the plurality of second wires (105) intersect at a portion between the first pumping chamber (101), the actuator (102) and the second chamber (102), the actuator (102). However, the same cannot be construed as a limitation as the plurality of first wires (104) and the plurality of second wires (105) may be wound around the first pumping chamber (101), the second pumping chamber (102) and the actuator (103) in any configuration such as spiral and the like, based on the requirement. The plurality of first wires (104) and the second wires (105) may be configured to selectively compress and decompress the first pumping chamber (101) and the second pumping chamber (102) corresponding to operation of the actuator (103) between the first operating position and the second operating position. That is, the plurality of first wires (104) and the plurality of second wires (105) may be configured to decompress the first pumping chamber (101) and the second pumping chamber (102) when the actuator (103) is at the first operating position (thus, deflated condition) for passively drawing the fluid into the first pumping chamber (101) and the second pumping chamber (102). Further, the plurality of first wires (104) and the plurality of second wires (105) are configured to compress the first pumping chamber (101) and the second pumping chamber (102), when the actuator (103) is at the second operating position (thus, inflated condition) for pumping the fluid out of the first pumping chamber (101) and the second pumping chamber (102).

In an embodiment, the first pumping chamber (101), the second pumping chamber (102) and the actuator (103) may be defined with a plurality of channels (107) on an outer surface. As an example, the plurality of channels (107) may be but not limiting to slots, grooves, tunnels, tubes and the like. The plurality of channels (107) may be configured to secure at least one first wire of the plurality of first wires (104) and at least one second wire of the plurality of second wires (105). Further, the plurality of channels (107) may be configured to guide the at least one first wire and the at least one second wire, relative to operation of the actuator (103) between the first operating state and the second operating state, to selectively compress and decompress the first pumping chamber (101) and the second pumping chamber (102), to create pulsatile flow of the fluid.

In an embodiment, the artificial heart (100) may include a control unit [not shown in figures], which may be communicatively coupled to the pump. The control unit may be configured to control operation of the pump to provide pulsatile flow of the driving fluid to the actuator (103). This configuration aids the artificial heart (100) to mimic heartbeat of the natural human heart.

In an embodiment, the first pumping chamber (101) and the second pumping chamber (102) may act as a right ventricle of a human heart and the second pumping chamber (102) may act as a left ventricle of the human heart, and the actuator (103) may act as a septum. The actuator (103) may be operated between its first operating position and the second operating position at desired interval, such that the first pumping chamber (101) and the second pumping chamber (102) decompress and compress corresponding to operation interval of the actuator (103), thereby mimicking pulsatile beating of the natural heart.

The configuration of the artificial heart (100) of the present disclosure makes the artificial heart (100) compact unlike conventional total artificial hearts which adapts heavy machined parts.

In an embodiment, the first pumping chamber (101) and the second pumping chamber (102) may include an inner layer or an outer layer. The inner layer which may contact the fluid may be made of biocompatible material and the outer layer may be made of soft, non-stretchable material.

In an operational embodiment, as seen in FIG. 1, the actuator (103) may be at the first operating position, where the actuator (103) is in a deflated condition. Due to deflation condition of the actuator (103), the plurality of first wires (104) and the plurality of second wires (105) may be in a state of slack, thereby exerting minimum or no pressure on the first pumping chamber (101) and the second pumping chamber (102). This results in the first pumping chamber (101) and the second pumping chamber (102) to be in the decompressed state, which may facilitate in passively drawing the fluid into the first pumping chamber (101) and the second pumping chamber (102). The fluid is drawn passively into the first pumping chamber (101) and the second pumping chamber (102) through the first inlet (108) and the second inlet (110), respectively, where the non-return valves (106) disposed in the first inlet (108) and the second inlet (110) are open, while the non-return valves (106) disposed in the first outlet (109) and the second outlet (111) are closed. As an example, in the installed condition of the artificial heart (100) within the human body, the first pumping chamber (101) may be configured to draw de-oxygenated blood from the body and the second pumping chamber (102) may be configured to draw oxygenated blood from the lungs. In an embodiment, the first pumping chamber (101) and the second pumping chamber (102) may continue to be in the decompressed state till the fluid is filled in the first pumping chamber (101) and the second pumping chamber (102). Upon filling of the fluid in the first pumping chamber (101) and the second pumping chamber (102), the actuator (103) may be operated from the first operating position to the second operating position [as seen in FIG. 3].

In the second operating position, the actuator (103) may be inflated leading to increase in surface area of the actuator (103). This may result in tightening the plurality of first wires (104) and the second wires (105) to exert force on the first pumping chamber (101) and the second pumping chamber (102), respectively. Due to exertion of forces, the first pumping chamber (101) and the second pumping chamber (102) may undergo compression, thereby exerting pressure on the fluid inside the first pumping chamber (101) and the second pumping chamber (102). This results in pumping of the stored fluid out of the first pumping chamber (101) and the second pumping chamber (102). As an example, in the installed condition of the artificial heart (100) within the human body, the first pumping chamber (101) may be configured to pump de-oxygenated blood into the lungs and the second pumping chamber (102) may be configured to pump oxygenated blood to the body. Further, the operation of selective compression and decompression of the first pumping chamber (101) and the second pumping chamber (102) may occur continuously for drawing and pumping the fluid (thus, the blood) in a pulsatile manner, thereby mimicking the function of the natural heart.

Figure 5A:
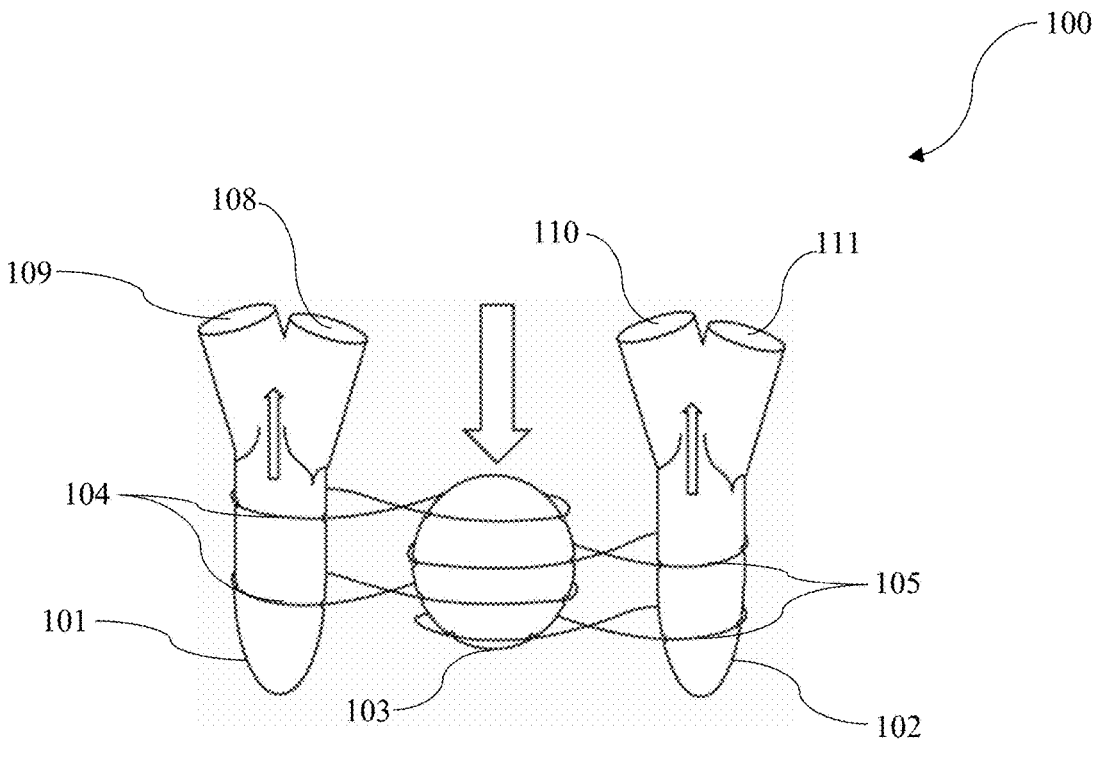
FIGS. 5a, 5b and 5c illustrates a schematic view of the implantable artificial heart, depicting the first operating state of the actuator, in accordance with another embodiment of the present disclosure.
Figure 5B:
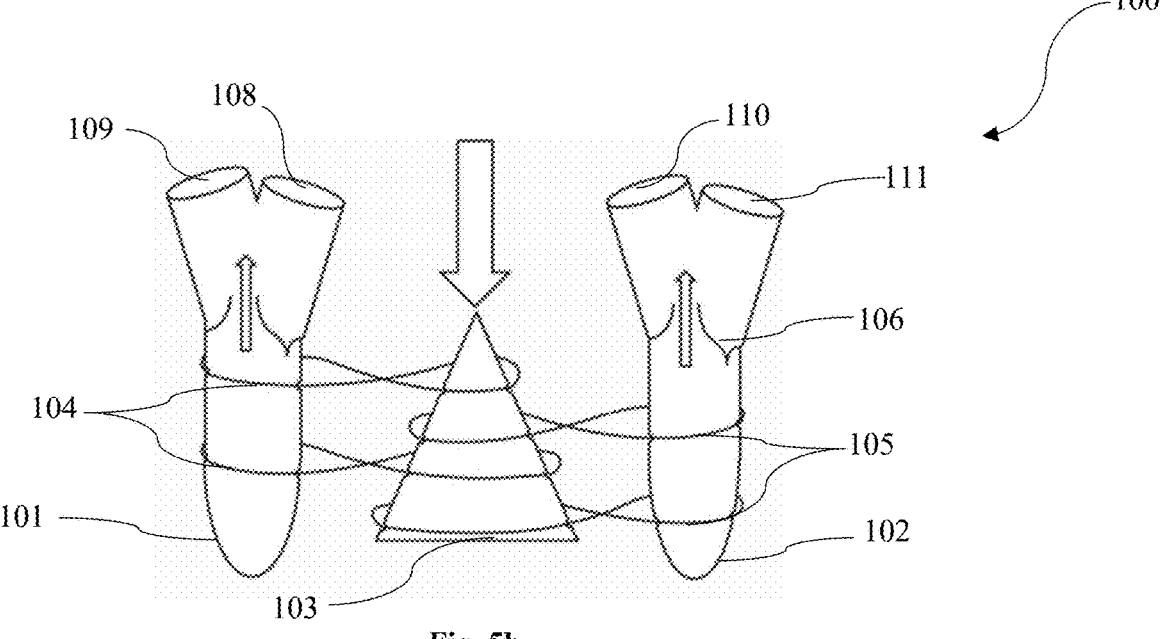
Figure 5C:
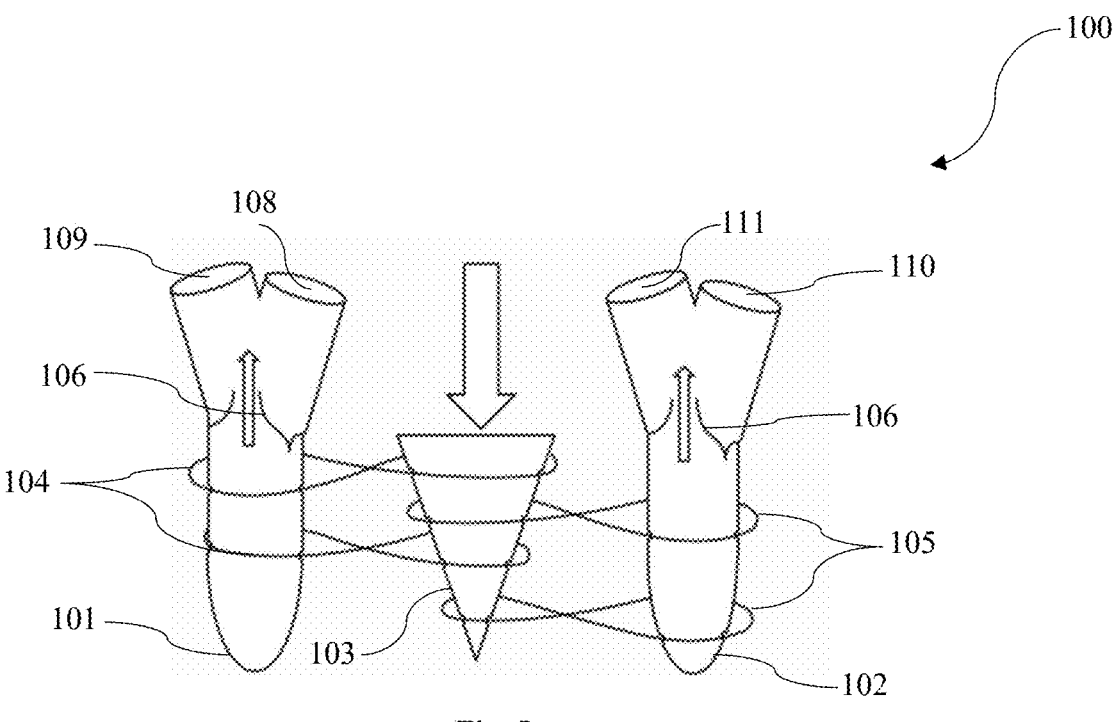

Turning now to FIGS. 5a-5c, which illustrate a schematic view of the implantable artificial heart (100), in accordance to another embodiment of the present disclosure. As seen in FIGS. 4a-4c The implantable artificial heart (100) may include first pumping chamber (101), a second pumping chamber (102) and an actuator (103) disposed between the first pumping chamber (101) and the second pumping chamber (102). Further, the artificial heart (100) may include a plurality of wires wound around the first pumping chamber (101) and the actuator (103), and a plurality of second wires (105) wound around the actuator (103) and the second pumping chamber (102). As seen in FIGS. 5a, 5b and 5c, the actuator (103) may include a circular profile, a triangular profile, an inverted triangular profile and the any other geometrical profile based on the requirement. Working of the artificial heart (100) depicted in FIGS. 5a-5c is similar to working of the artificial heart (100) as described with respect to FIGS. 1-4.

Figure 6A:
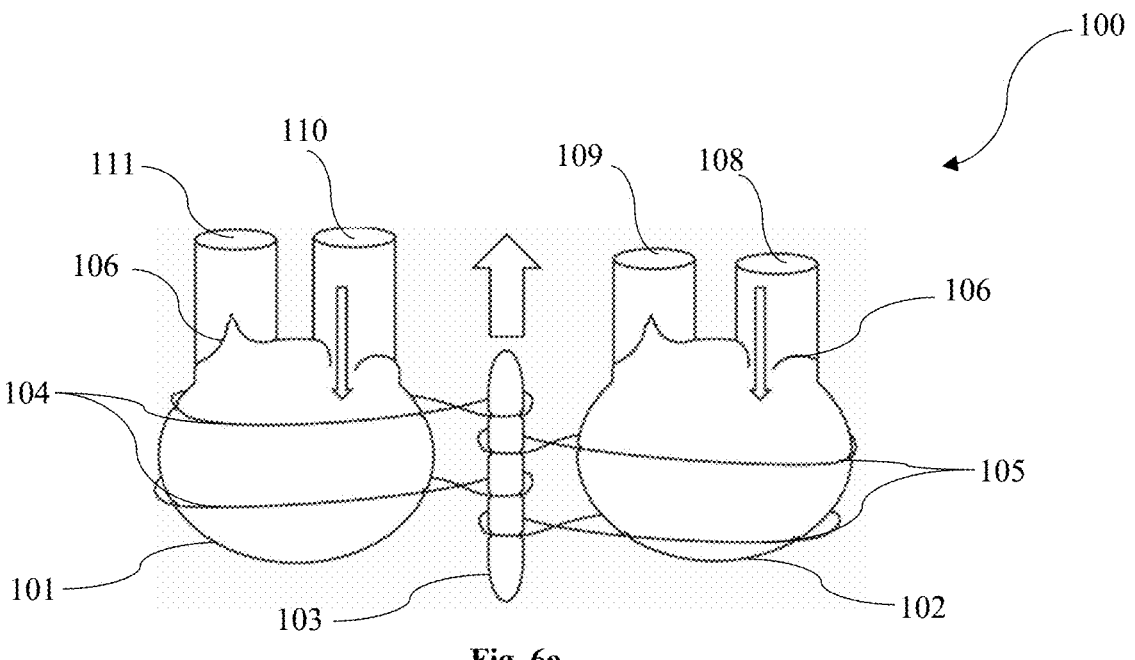
FIGS. 6a, 6b and 6c illustrates a schematic view of the implantable artificial heart, depicting the first operating state of the actuator, in accordance with another embodiment of the present disclosure.
Figure 6B:
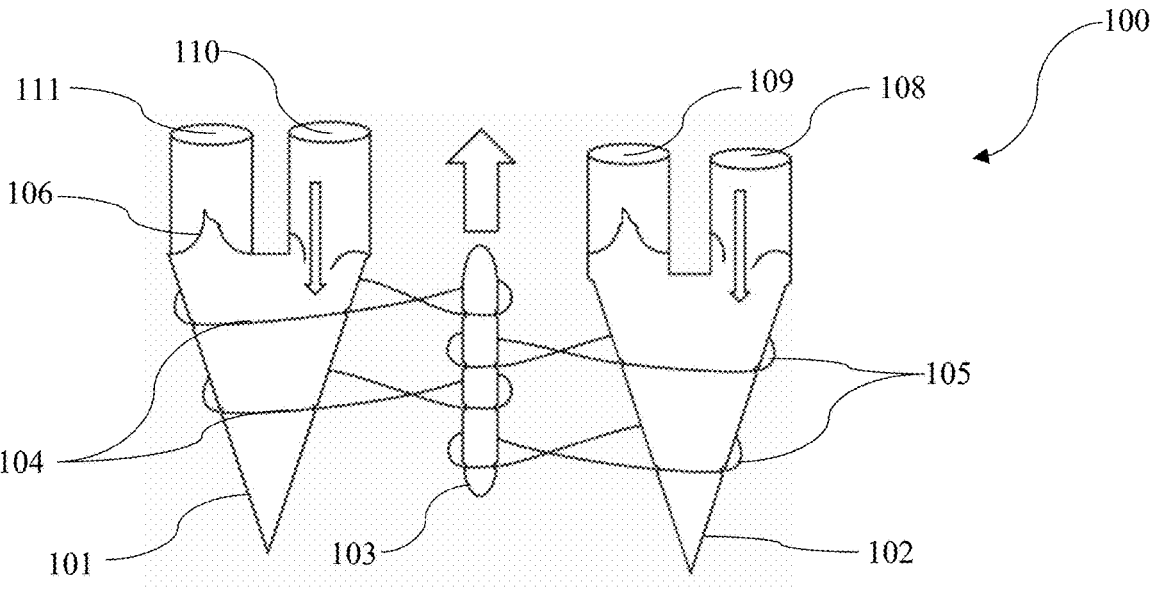
Figure 6C:
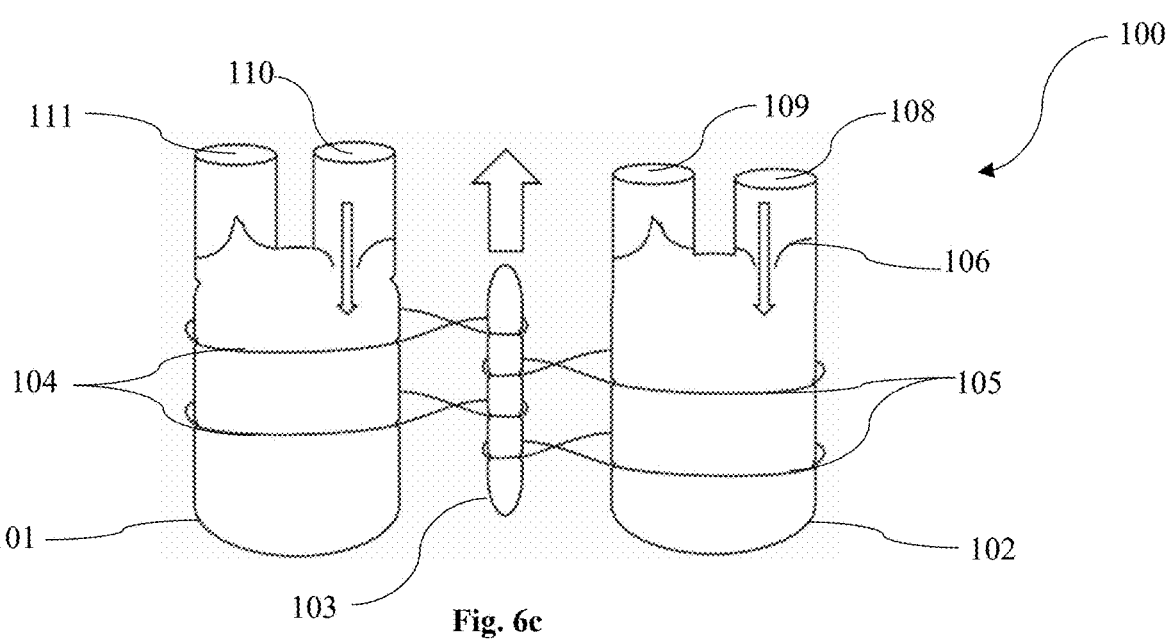

Referring now to FIGS. 6a-6c, which illustrate a schematic view of the implantable artificial heart (100), in accordance to another embodiment of the present disclosure. As seen in FIGS. 6a-6c, the implantable artificial heart (100)

may include first pumping chamber (101), a second pumping chamber (102) and an actuator (103) disposed between the first pumping chamber (101) and the second pumping chamber (102). Further, the artificial heart (100) may include a plurality of wires wound around the first pumping chamber (101) and the actuator (103), and a plurality of second wires (105) wound around the actuator (103) and the second pumping chamber (102). As seen in FIGS. 6a-6c, the first pumping chamber (101) and the second pumping chamber (102) may include a bowl profile, an inverted triangular profile and a triangular profile. Working of the artificial heart (100) depicted in FIGS. 6a-6c similar to working of the artificial heart (100) as described with respect to FIGS. 1-4.

Example

Various experiments have been conducted on the implantable total artificial heart of the present disclosure. The implantable total artificial heart is subjected to several in-vitro tests. In one exemplary iteration of the test, it was found that the implantable total artificial heart can pump 5.7 l/min of cardiac output under normal hemodynamic conditions in-vitro. Also it was found that, the beat rates ranged between 60 to 80 bpm. Further, it was also noted that the implantable total artificial heart is preload dependent, i.e., stroke volume (volume of blood pumped from the ventricle implantable total artificial heart per beat), increases when the preload increases, and the same is comparable to the native human heart. Furthermore, it is also found that the implantable total artificial heart is somewhat afterload dependent. Afterload is the pressure that the heart must work against to eject blood during ventricular contraction.

The implantable total artificial heart has been subjected to in-vitro experiments in a mock circulation loop (MCL) developed based on wind-kessel model. The mock circulation loop mimics various systemic and pulmonary afterloads and preloads, as well as systemic and pulmonary peripheral resistances and compliance of a human heart.

In another iteration and also to determine preload sensitivity of the implantable total artificial heart its preloads ranged from 4 mmHg to 18 mmHg. The preload is adjusted using the MCL setup filled with tap water. A tube was placed between the two preload tanks as a shunt to maintain same fluid levels in both tanks. After testing each preload setting, the preload pressure is raised using increments of 1 mmHg by adding more tap water to the preload tanks. For each preload value, three runs consisting of 25 to 30 beats were performed using a beat rate of 60 beats per minute (BPM) and a systole time of 0.35 seconds. Pulmonary and systemic afterloads were kept constant at mean pressures of 25 mmHg and 90 mmHg, respectively. Due to changes in stroke volume at different preload values, the resistor valves is adjusted during the experiment to maintain constant afterloads. Mean stroke volumes have been calculated based on 6 beats for each 3 runs, thus 18 beats in total for each preload increment. To determine afterload sensitivity of the implantable total artificial heart, mean left afterloads ranging between 50-120 mmHg have been adjusted using the MCL setup filled with tap water. A shunt was placed between the two preload tanks and the total volume of water in the system was kept constant. The test has been conducted in a single run during which the left afterload was increased in increments of approximately 10 mmHg by adjusting the resistor element mimicking the systemic resistance. For each afterload, approximately 30-40 beats were captured at a beat rate of 60 beats per minute and systole time (time period in which ventricular contraction takes place) of 0.3 seconds.

The preloads (6 mmHg) and pulmonary resistor element were kept constant. Mean stroke volumes were calculated based on 3 sections of 6 beats, thus 18 beats in total for each afterload increment. Further variable heart beat rate test has been conducted to determine the influence of various beat rates (30-100 BPM) to cardiac outputs. The MCL was filled with tap water and a shunt was placed between two preload tanks. The test was started at 60 BPM and 0.30 s systole time, the optimal condition in respect to pulse pressure, stroke volume and generated afterloads. This test determined the settings of the pulmonary and systemic peripheral resistors. Afterwards, we tested all beat rates (30-100 BPM and 0.30 s sytole time) without changing the resistors. Mean stroke volumes were calculated based on 10 beats for each run.

It was found that the implantable total artificial heart can obtain a maximum cardiac output of 5.7 L/min on the left side and 5.0 L/min on the right side under physiological hemodynamic conditions (table 1, FIG. 1). Deliberately, it was aimed for higher cardiac outputs of the left ventricle compared to the right ventricle. This is due to the high aortic pressure (left afterload) compared to the pulmonary artery pressure (right afterload) and the shunting of some blood ejected by the left ventricle that returns directly to the left ventricle, via the bronchial circulation. It was able to increase the left cardiac output relatively to the right cardiac output by adjusting the length of wires around the right ventricle.

The human heart balances its cardiac output by the Frank-Starling mechanism. When the venous return (preload) rises in the human heart, its contractile force increases resulting in increased stroke volume. The implantable total artificial heart needs to have a similar mechanism that allows for increased cardiac output when the preload increases, otherwise severe complications occur.

Ideally, such a mechanism should work passively, to avoid the use of bulky hardware and sensors that are also prone to failure. In the implantable total artificial heart, soft materials have been used and the design in which the ventricles are not fully expanded and filled at the end of diastole in normal operation, which intrinsically add compliance to the ventricles. It is found that the implantable total artificial heart is sensitive to preload changes and increases stroke volume passively when venous return increases (FIGS. 7a-7f). For each mmHg of preload rise, the implantable total artificial heart ejects 198 ml/min extra. This is in the range of the native human heart (241 ml/min/mmHg) (see FIG. 7a-7f). For each mmHg afterload rise, the left ventricle ejects 20 ml/min less, which is less afterload sensitive than the human heart (41 ml/min/mmHg). The lower the afterload sensitivity of the implantable total artificial heart, the better, to ensure sufficient cardiac output in a wide range of afterloads. Relevant experimental results obtained have been captured in form of graphical representations in FIGS. 7a-7f.

Figure 7A:
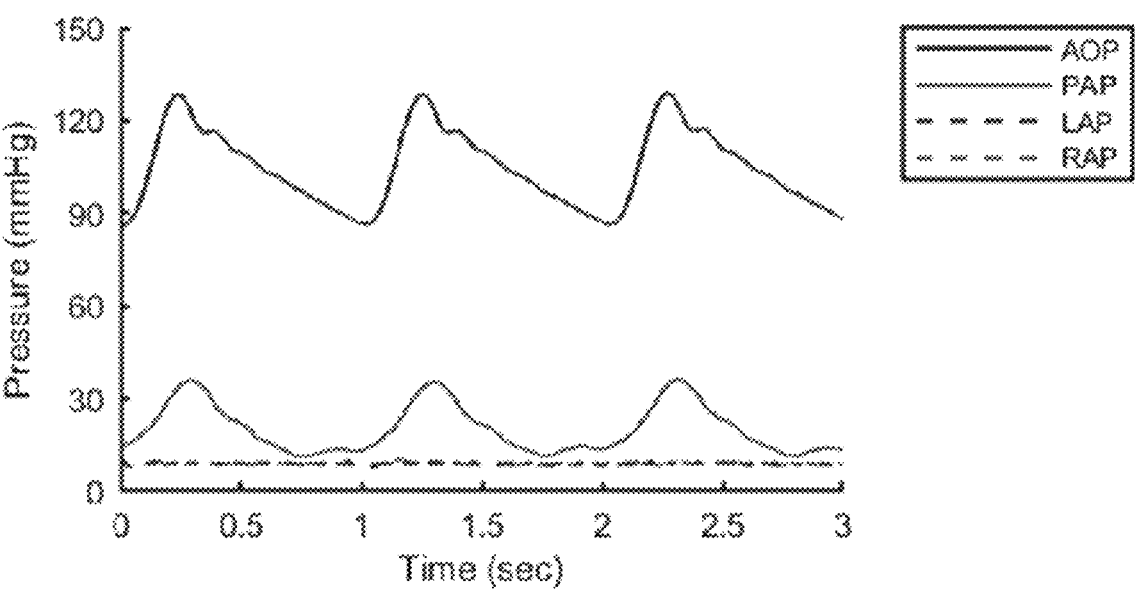
FIGS. 7a-7f show graphical representations of experimental results.
Figure 7B:
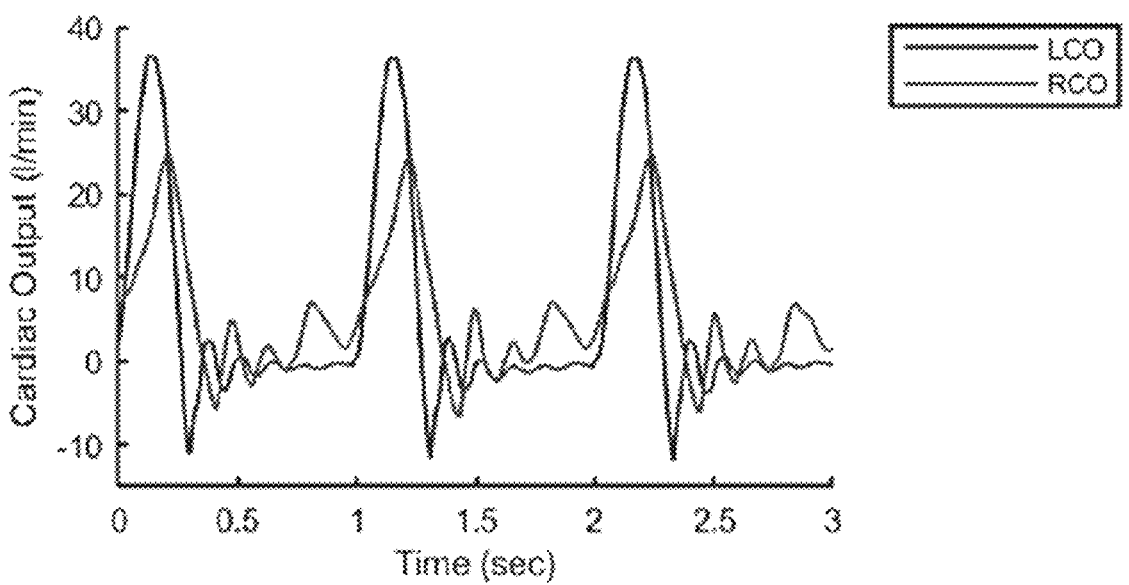
Figure 7C:
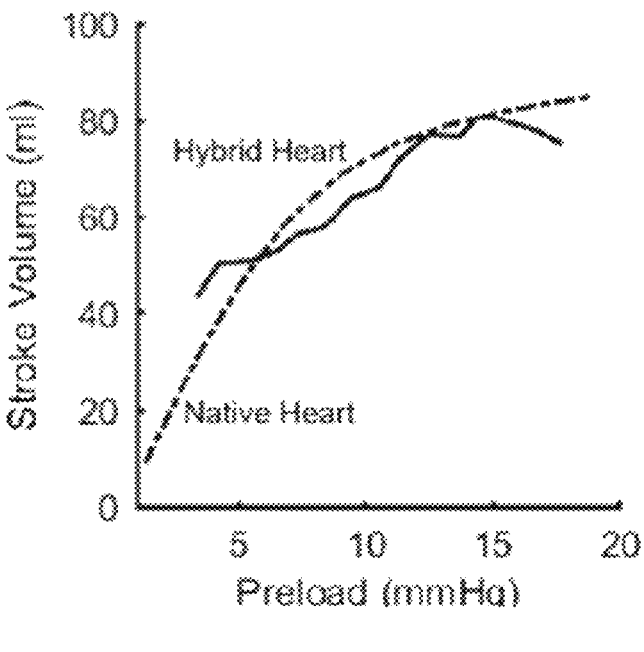
Figure 7D:
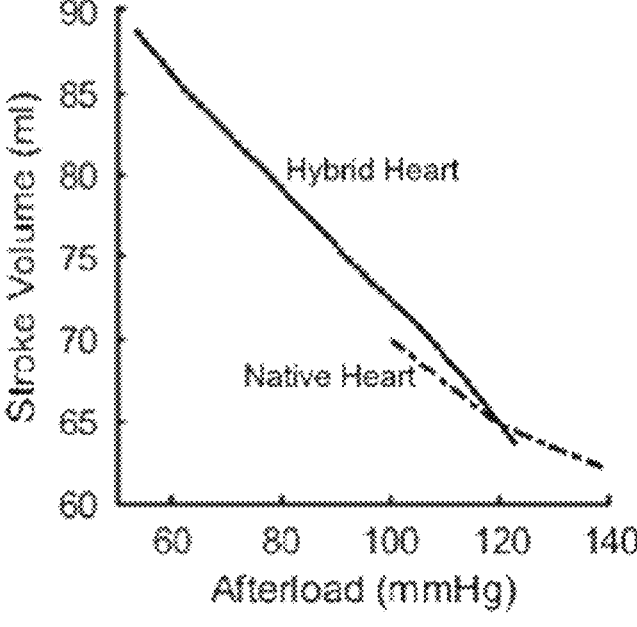
Figure 7E:
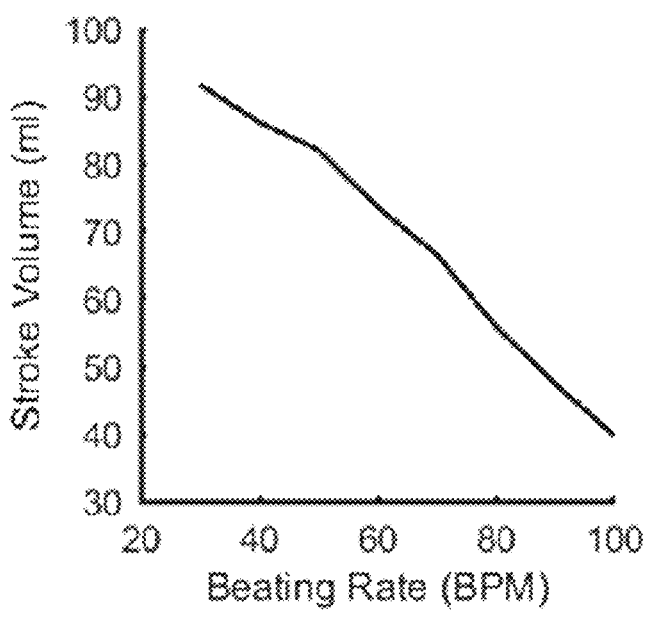
Figure 7F:
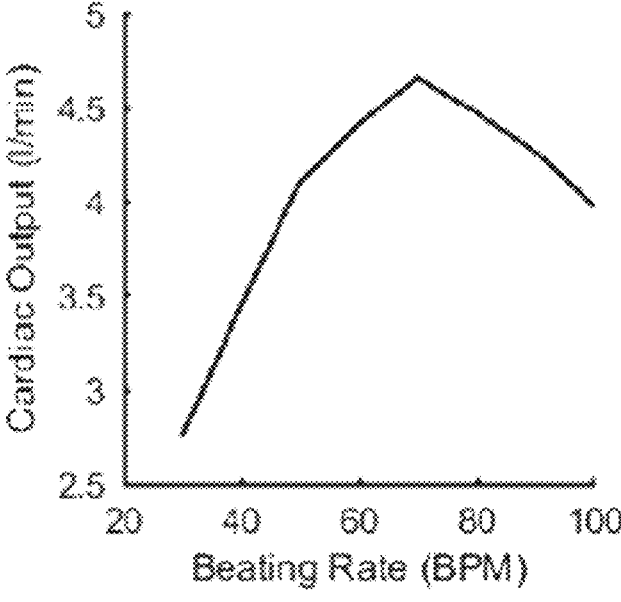

FIG. 7a shows Pressure curves measured during implantable total artificial heart operation in the mock circulatory loop. AOP=aortic pressure, PAP=pulmonary artery pressure, LAP=left atrial pressure, RAP=right atrial pressure. FIG. 7b shows cardiac output curves measured during implantable total artificial heart operation in the mock circulatory loop. LCO=Left cardiac output, RCO=right cardiac output FIG. 7c The relation between varying left preload versus left stroke volume, measured during implantable total artificial heart operation in the mock circulatory loop (continuous line) resembles native heart preload sensitivity (dashed line). FIG. 7d shows the relation between varying systemic afterload versus left stroke volume, measured during implantable total artificial heart operation in the mock circulatory loop (continuous line), versus native heart (dashed line). FIG. 7e shows the relation between varying beat rate versus left stroke volume, measured during implantable total artificial heart operation in the mock circulatory loop. Higher beat rates decrease stroke volume. FIG. 7f shows the relation between varying beat rate versus left cardiac output, measured during implantable total artificial heart operation in the mock circulatory loop. Optimal performance is obtained between 60-80 bpm.

Furthermore, studies were done to check on the influence of wire arrangements on the ventricles output during various tests in the double circulatory mock loop. The implantable total artificial heart the right stroke volume is decreased compared to the left stroke volume by changing the wire length of the right ventricle. Testing has been done on three prototypes, which were exact copies of each other. First, we have tested these prototypes with similar wire configurations, and similar wire length for both ventricles. Each ventricle had 5 wires run in parallel, spaced apart with similar distances. We tested these prototypes in the double circulatory mockloop under physiological conditions, where we noticed that the measured stroke volumes varied per prototype (Table 1). The left stroke volumes were 76, 68 and 91 ml respectively for the three prototypes and the right stroke volumes were 84, 76 and 125 ml respectively. Furthermore, it should be noted that with similar wire configurations for the left and right ventricle, all three prototypes had larger right ventricular outputs compared to the left. The right sided stroke volumes by loosening the wires of the right ventricle. This would result in complete filling of the right ventricle, and reduced ejection. It was found that, with loosening the wires, we could successfully decrease the right sided stroke volume to 79, 66 and 83 ml respectively (Table 1). By loosening the wires of the right ventricle, the stroke volume of the left ventricle increased in all cases, 79, 84 and 95 ml respectively (Table 1).

TABLE 1

| | Similar configuration left and right ventricles | | | | | | Loosening wires of the right ventricle | | | | | |
| --- | --- | --- | --- | --- | --- | --- | --- | --- | --- | --- | --- | --- |
| | SV L ml | SV R ml | CO L l/min | CO R l/min | Aft L mmHg | Aft R mmHg | SV L ml | SV R ml | CO L l/min | CO R l/min | Aft L mmHg | Aft R mmHg |
| V1 | 76 | 84 | 4.5 | 5.0 | 98 | 30 | 79 | 79 | 4.7 | 4.7 | 100 | 27 |
| V2 | 68 | 76 | 4.1 | 4.6 | 85 | 32 | 84 | 66 | 5.0 | 3.9 | 89 | 26 |
| V3 | 91 | 125 | 5.5 | 7.5 | 100 | 27 | 95 | 83 | 5.7 | 5.0 | 105 | 20 |

SV = stroke volume.
L = left.
R = right.
CO = cardiac output.
Aft = afterload.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances, where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." While various aspects and embodiments have been disclosed herein, other aspects and embodiments will be apparent to those skilled in the art. The various aspects and embodiments disclosed herein are for purposes of illustration and are not intended to be limiting.

REFERRAL NUMERALS

| Reference Number | Description |
|---|---|
| 100 | Implantable artificial heart |
| 101 | First pumping chamber |
| 102 | Second pumping chamber |
| 103 | Actuator |
| 104 | First wires |
| 105 | Second wires |
| 106 | Non-return valves |
| 107 | Channels |
| 108 | First inlet |
| 109 | First outlet |
| 110 | Second inlet |
| 111 | Second outlet |

The invention claimed is:

1. An implantable total artificial heart, the artificial heart comprising:
a first pumping chamber defined with a first inlet and a first outlet;
a second pumping chamber positioned adjacent to the first pumping chamber and defined with a second inlet and a second outlet;
an actuator disposed between the first pumping chamber and the second pumping chamber, wherein the actuator is configured to be operated between a first operating state and a second operating state;
a plurality of first wires wound around the first pumping chamber and the actuator, wherein the plurality of first wires are configured to selectively decompress and compress the first pumping chamber as a result of operation of the actuator between respectively the first operating state and the second operating state for respectively drawing fluid into and pumping fluid out of the first pumping chamber; and
a plurality of second wires wound around the second pumping chamber and the actuator,
wherein the plurality of second wires are configured to selectively decompress and compress the second pumping chamber as a result of operation of the actuator between respectively the first operating state and the second operating state for respectively drawing fluid into and pumping fluid out of the second pumping chamber,
wherein the first operating state corresponds to a deflated condition of the actuator causing a decompressed state of both the first pumping chamber and the second pumping chamber for passive drawing of the fluid into the first pumping chamber and the second pumping chamber, and
wherein the second operating state corresponds to an inflated condition of the actuator causing a compressed state of both the first pumping chamber and the second pumping chamber for pumping the fluid out of the first pumping chamber and the second pumping chamber.

2. The artificial heart of claim 1, comprising at least one non-return valve disposed in each of the first inlet, the first outlet, the second inlet and the second outlet.

3. The artificial heart of claim 1, wherein an outer surface of the first pumping chamber, the second pumping chamber and the actuator is defined with a plurality of channels.

4. The artificial heart of claim 3, wherein each of the plurality of channels is configured to secure at least one first wire of the plurality of first wires and at least one second wire of the plurality of second wires.

5. The artificial heart of claim 4, wherein each of the plurality of channels is configured to guide the at least one first wire and the at least one second wire, relative to operation of the actuator between the first operating state and the second operating state.

6. The artificial heart of claim 1, wherein the first pumping chamber and the second pumping chamber are configured to store the fluid.

7. The artificial heart of claim 1, wherein the first pumping chamber and the second pumping chamber are made of fluid tight, non-stretchable material.

8. The artificial heart of claim 1, wherein an inner surface of the first pumping chamber and the second pumping chamber is made of biocompatible material.

9. The artificial heart of claim 1, comprising a pump fluidly coupled to the actuator, wherein the pump is configured to selectively operate the actuator between the first operating state and the second operating state in a pulsating manner.

10. The artificial heart of claim 9, comprising a control unit communicatively coupled to the pump, wherein the control unit is configured to control actuation of the pump to provide pulsatile flow of driving fluid or driving gas to the actuator.

11. The artificial heart of claim 1, wherein the plurality of first wires are wound around the first pumping chamber and the actuator in a crisscross configuration, wherein the plurality of first wires intersect at a portion between the first pumping chamber and the actuator.

12. The artificial heart of claim 11, wherein the plurality of second wires are wound around the second pumping chamber and the actuator in a crisscross configuration, wherein the plurality of second wires intersect at a portion between the second pumping chamber and the actuator.

13. The artificial heart of claim 1, wherein the plurality of second wires are wound around the second pumping chamber and the actuator in a crisscross configuration, wherein the plurality of second wires intersect at a portion between the second pumping chamber and the actuator.

* * * * *